(12) United States Patent
Troxell

(10) Patent No.: US 12,611,140 B2
(45) Date of Patent: Apr. 28, 2026

(54) MEDICAL IMPLANTS WITH CIRCUITS TREATING PERIPROSTHETIC JOINT INFECTION AND OTHER SENSING

(71) Applicant: GLOBUS MEDICAL, INC., Audubon, PA (US)

(72) Inventor: Paden Troxell, Conshohocken, PA (US)

(73) Assignee: Globus Medical, Inc., Audubon, PA (US)

( * ) Notice: Subject to any disclaimer, the term of this patent is extended or adjusted under 35 U.S.C. 154(b) by 321 days.

(21) Appl. No.: 18/322,190

(22) Filed: May 23, 2023

(65) Prior Publication Data

US 2024/0389939 A1    Nov. 28, 2024

Related U.S. Application Data

(63) Continuation of application No. 18/322,125, filed on May 23, 2023.

(51) Int. Cl.
| | |
|---|---|
| *A61B 5/00* | (2006.01) |
| *A61B 7/00* | (2006.01) |
| *A61N 1/05* | (2006.01) |
| *A61N 1/08* | (2006.01) |
| *A61F 2/30* | (2006.01) |

(52) U.S. Cl.
CPC .......... *A61B 5/4851* (2013.01); *A61B 5/0008* (2013.01); *A61B 5/4836* (2013.01); *A61B 5/686* (2013.01); *A61B 7/005* (2013.01); *A61N 1/05* (2013.01); *A61N 1/08* (2013.01); *A61B 2562/0219* (2013.01); *A61F 2002/3067* (2013.01)

(58) Field of Classification Search
CPC . A61B 2562/0219; A61B 5/0008; A61B 5/01; A61B 5/112; A61B 5/1473; A61B 5/4528; A61B 5/4836; A61B 5/4851; A61B 5/6843; A61B 5/686; A61B 7/005; A61F 2/30; A61F 2/482; A61F 2002/30668; A61F 2002/3067; A61F 2002/30677; A61N 1/05; A61N 1/08; A61N 1/3787
See application file for complete search history.

(56) References Cited

U.S. PATENT DOCUMENTS

2015/0073491 A1*  3/2015  Ehrensberger ............ A61L 2/24
607/116

* cited by examiner

*Primary Examiner* — Amanda K Hulbert

(57)                ABSTRACT

A medical implant includes an implant component configured to be implanted in a patient, an electrode array, an energy storage device, and a power management unit. The electrode array includes at least two electrodes spaced apart on the implant component. The energy storage device and power management unit are inside the implant component. The power management unit is operative to control electrical stimulation of the electrode array by current supplied by the energy storage device to be at a level which at least reduces formation of a biofilm on at least part of the implant component while implanted in the patient.

10 Claims, 9 Drawing Sheets

MEDICAL IMPLANTS WITH CIRCUITS TREATING PERIPROSTHETIC JOINT INFECTION AND OTHER SENSING

CROSS-REFERENCE TO RELATED APPLICATIONS

This application is a continuation application of U.S. patent application Ser. No. 18/322,125 filed on May 23, 2023, which is incorporated in its entirety herein.

FIELD

The present disclosure relates to medical implants, such as for joint arthroplasty.

BACKGROUND

Periprosthetic joint infection (PJI) is one of the most feared complications in joint arthroplasty due to the ineffectiveness of antibiotics, invasive treatment options, and a relatively high annual mortality rate of 4%. If caught early enough, antibiotics and natural immune responses are very effective at intercepting the free-floating bacteria within the surgical site. However, antibiotics are remarkably ineffective at eradicating bacteria within biofilm on the surface of the implant.

Biofilm develops as bacteria adhere to and colonize on the surface of an implant. The biofilm layer serves as a biochemical fortress that prevents penetration of antibiotic agents. It has been reported that 500-5000 times the concentration of antibiotics are required to have the same effectiveness on biofilm bacteria as compared to free-floating planktonic bacteria. As a result, the most common treatment for PJI is highly invasive two-stage revision.

Two-stage revision involves an initial operation to remove the septic implant and debride the surgical site and a second procedure to place new implant components. Although two-stage revision is the most common treatment option for PJI, the success rate has been reported to be a mere 85%. In addition, the risk of reinfection following revision for PJI has been reported to be 9% compared to 1-2% following the primary procedure. Also, the annual mortality rate has been reported to be as high as 14% following two-stage revision.

Much of the research and product development activity has been focused on preventing, rather than treating, infection following joint arthroplasty. Despite the incorporation of prevention strategies, including sterilization standards, shorter operative times, laminar airflow systems, body exhaust suits, perioperative antibiotics, antibiotic cement, and antimicrobial adhesive dressings, the incidence of PJI after THA and TKA has remained relatively constant over the past 20 years. This lack of improvement is likely due in part to the ineffectiveness of these solutions in preventing and eradicating the pathogenesis of joint infection, which is the formation of biofilm.

SUMMARY

Some embodiments of the present disclosure are directed to a medical implant that includes an implant component configured to be implanted in a patient, an electrode array, an energy storage device, and a power management unit. The electrode array includes at least two electrodes spaced apart on the implant component. The energy storage device and power management unit are inside the implant component. The power management unit is operative to control electrical stimulation of the electrode array by current supplied by the energy storage device to be at a level which at least reduces formation of a biofilm on at least part of the implant component while implanted in the patient.

Some further embodiments are directed to the power management unit being operative to control current density through patient tissue between the at least two electrodes of the electrode array while the electrode array is electrically stimulated by the energy storage device. The medical implant can include a controller operative to control duration of the electrical stimulation of the electrode array by the power management unit. Some further embodiments are directed to arrangements of electrodes of the electrode array and to sensors providing data for reporting and which may result in the controller initiating therapeutic electrical stimulation of the electrode array.

Some other embodiments are directed to a network computing resource that includes a network interface, processor, and memory storing instructions executable by the processor to perform operations. The operations include obtaining sensor data from at least one sensor of a medical implant within a patient, and providing to a display device indications of values of the sensor data. The operations communicate an activation command through the network interface addressed to a controller of the medical implant and are configured to initiate electrical stimulation by the controller of an electrode array at a level which at least reduces formation of a biofilm on at least part of an implant component while implanted in the patient.

Other medical implants, network computing resources, and corresponding methods according to embodiments of the present disclosure will be or become apparent to one with skill in the art upon review of the following drawings and detailed description. It is intended that all such additional medical implants, network computing resources, and methods be included within this description, be within the scope of the present inventive subject matter, and be protected by the accompanying claims. Moreover, it is intended that all embodiments disclosed herein can be implemented separately or combined in any way and/or combination.

DESCRIPTION OF THE DRAWINGS

Aspects of the present disclosure are illustrated by way of example and are not limited by the accompanying drawings. In the drawings.

Figure 6:
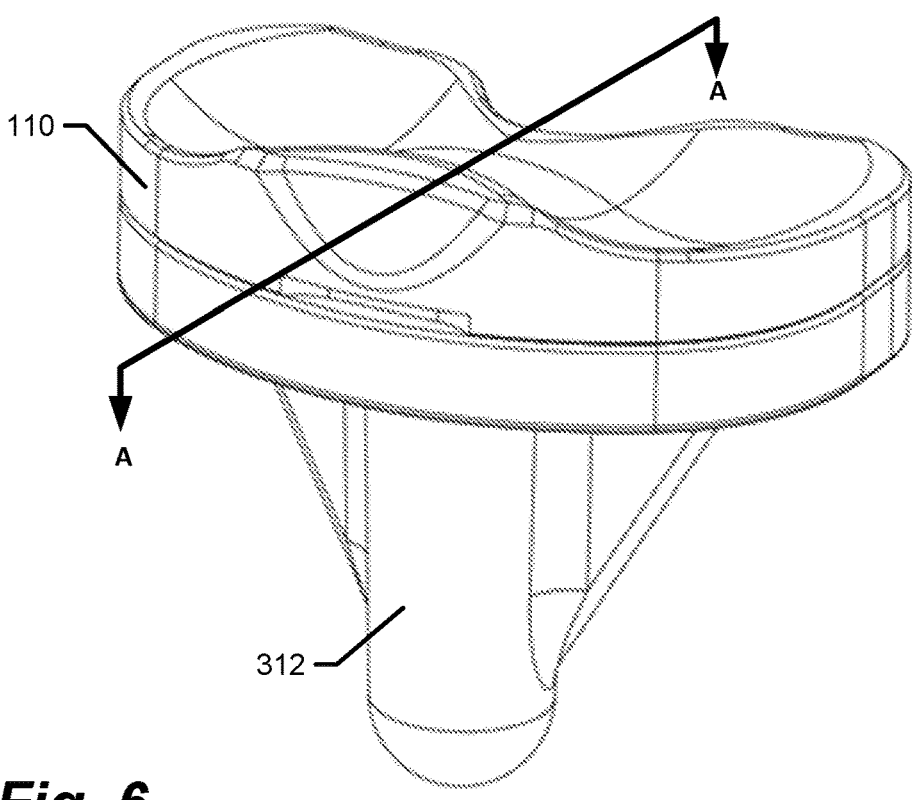
Figure 7:
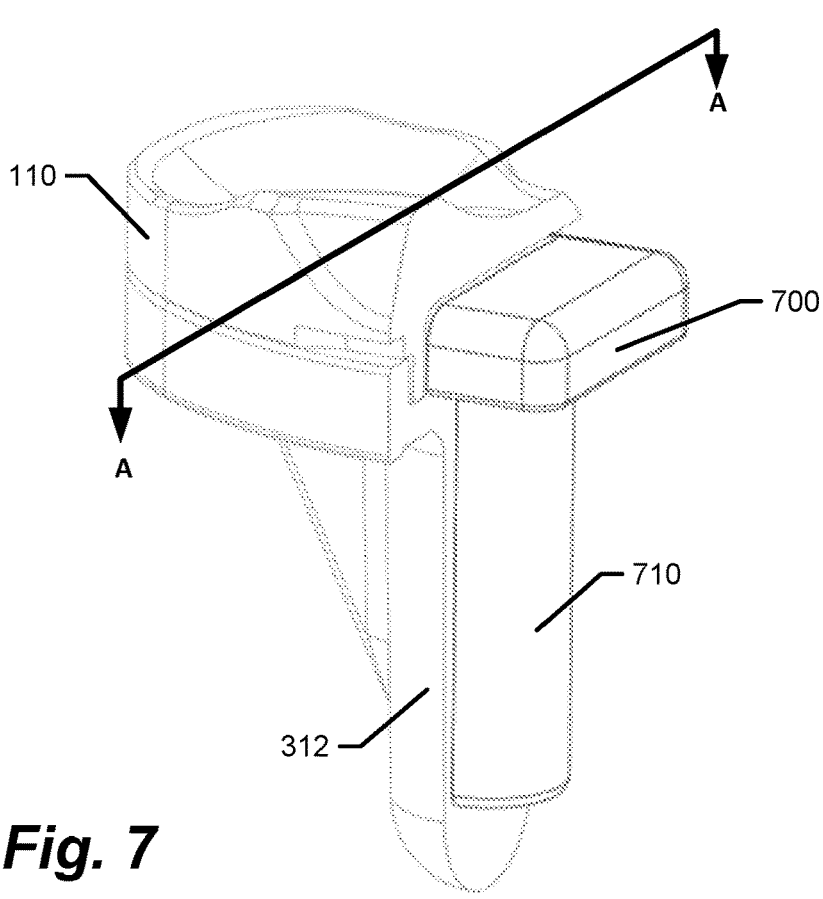
Figure 8:
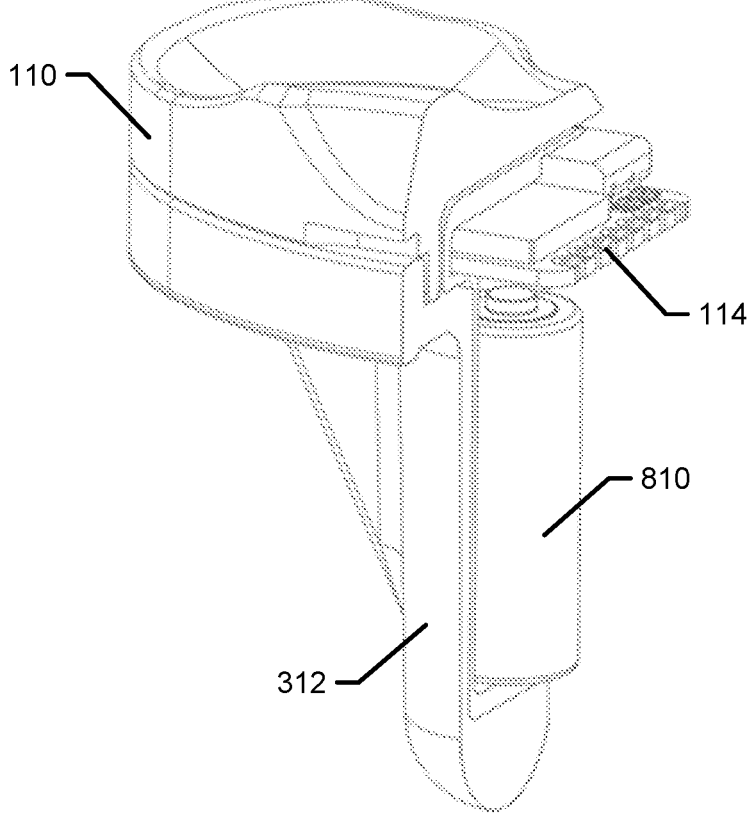
Figure 9A:
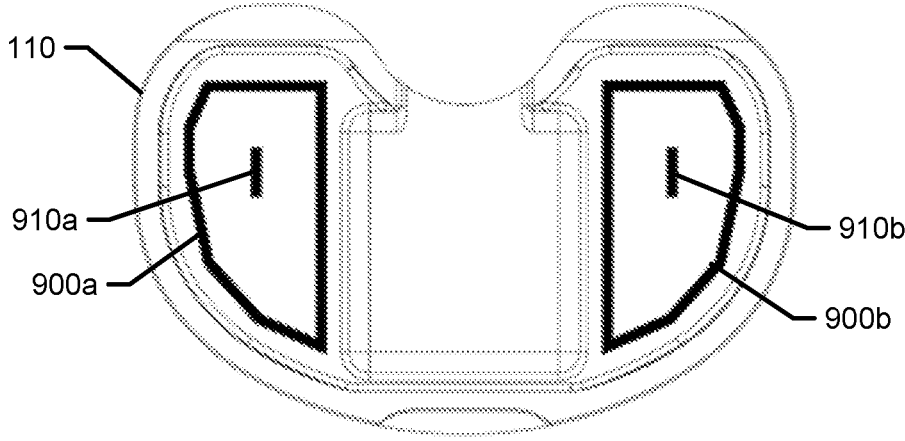
Figure 9B:
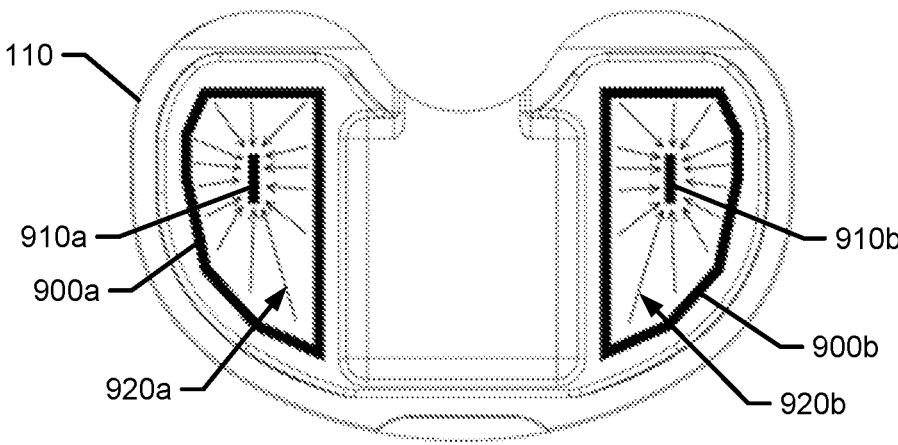
Figure 10:
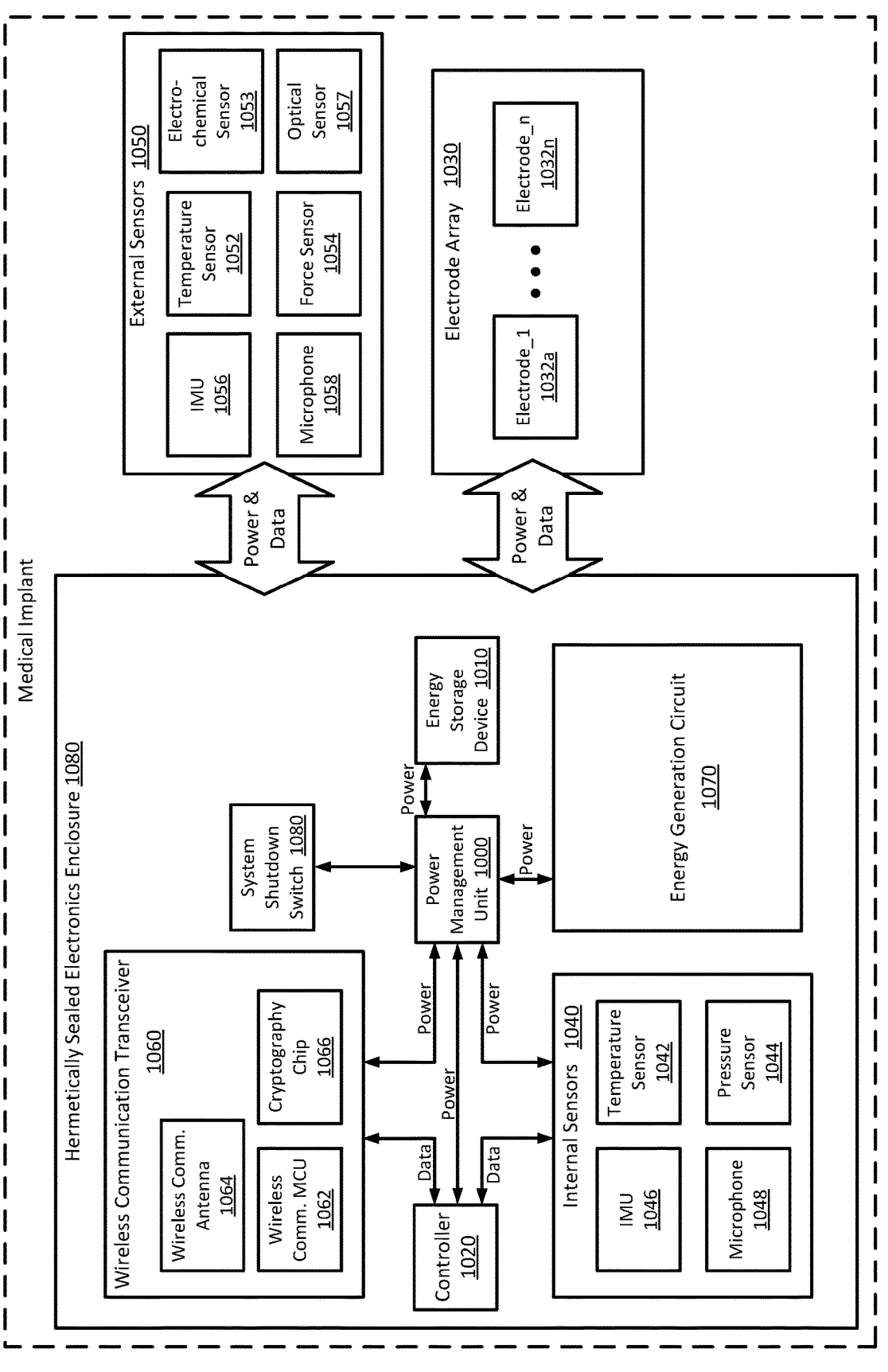
Figure 11:
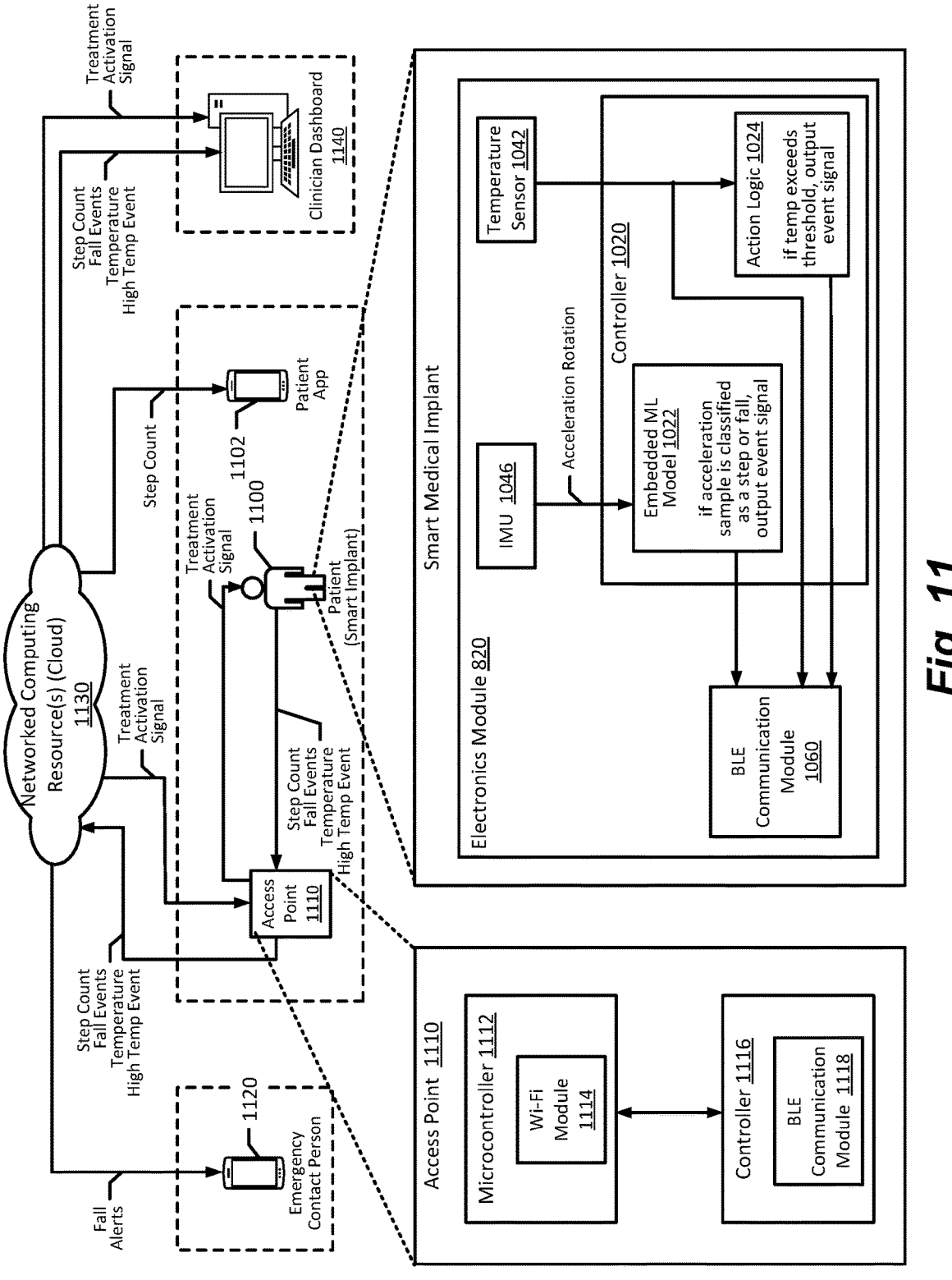

illustrates an isometric view of the tibial insert showing a cross-sectional line A-A which extends through an embedded energy storage device and electronics which operate according to some embodiments of the present disclosure;

FIG. 7 illustrates a cross-sectional view along line A-A of the tibial insert of FIG. 6 which exposes two sealed enclosures collectively containing an embedded energy storage device and electronics including a power management unit, controller, and sensors according to some embodiments of the present disclosure;

FIG. 8 illustrates the tibial insert of FIG. 7 with the enclosures removed to expose an arrangement of the embedded energy storage device and electronics including a power management unit, controller, and sensors according to some embodiments of the present disclosure;

FIG. 9A illustrates a top view of the component of the tibial insert of FIG. 6 with a pair of tibial trays in which pairs of electrodes are formed, according to some embodiments of the present disclosure;

FIG. 9B illustrates electrical fields extending between the electrodes of FIG. 9A while electrically stimulated, according to some embodiments of the present disclosure;

FIG. 10 illustrates components of a medical implant which are interconnected and configured to operate according to some embodiments of the present disclosure; and FIG. 11 illustrates a system that includes a network computing resource 1130, wireless communication access point 110, medical implant and other elements which are interconnected and configured to operate according to some embodiments of the present disclosure.

DETAILED DESCRIPTION

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Some embodiments of the present disclosure are directed to joint reconstruction implants that have electronic circuits ("smart implants") which are operate to provide surgeons and/or their patients the operational ability to monitor, detect, and diagnose Periprosthetic Joint Infection (PJI). Smart implants can be further operative to reduce or prevent and eradicate PJI through operation of the electronic circuits, and may increase the effectiveness of antibiotics and reduce the prevalence of two-stage revision procedures.

Figure 1:
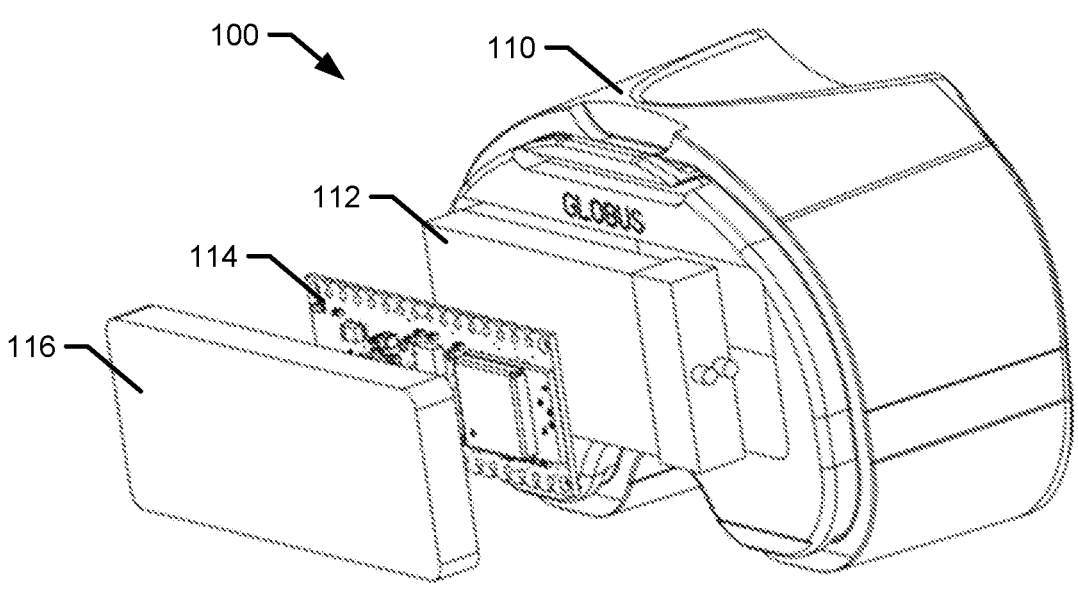
FIG. 1 illustrates an exploded isometric view of some components of a knee replacement implant that is operative to control electrical stimulation of an electrode array to at least reduce formation of a biofilm while implanted in a patient, according to some embodiments of the present disclosure.

FIG. 1 illustrates an exploded isometric view of some components of a knee replacement implant 100 that is operative to control electrical stimulation of an electrode array to at least reduce formation of a biofilm while implanted in a patient, according to some embodiments of the present disclosure.

Referring to FIG. 1, the knee replacement implant 100 includes a component 110 of a tibial insert on which are mounted an electrode array (See FIGS. 4B, 5B) comprising at least two electrodes spaced apart on the implant component 110, an energy storage device 112 (e.g., rechargeable battery), electronics 114, and an enclosure 116 adapted to hermetically seal electronics 114 and energy storage device 112 to the support 110 while implanted in the patient.

Figure 2:
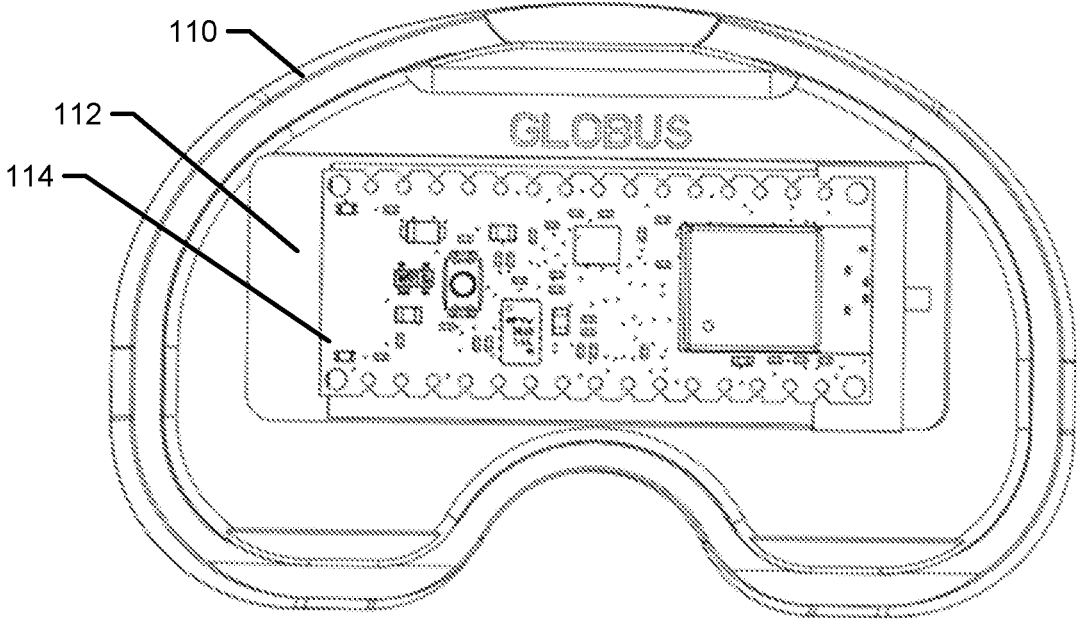
FIG. 2 illustrates a top view of the component of the tibial insert of FIG. 1 showing electronics including a power management unit and a controller which are operative according to some embodiments of the present disclosure.

FIG. 2 illustrates a top view of the component 110 of the tibial insert of FIG. 1 showing electronics 114 which includes a power management unit and a controller which are operative to at least reduce formation of a biofilm on at least part of the support 110 while implanted in the patient and to sense various characteristics according to some embodiments of the present disclosure. The controller may include one or more processor circuits ("processor") which execute instructions stored in one or more memory circuits ("memory").

Figure 3A:
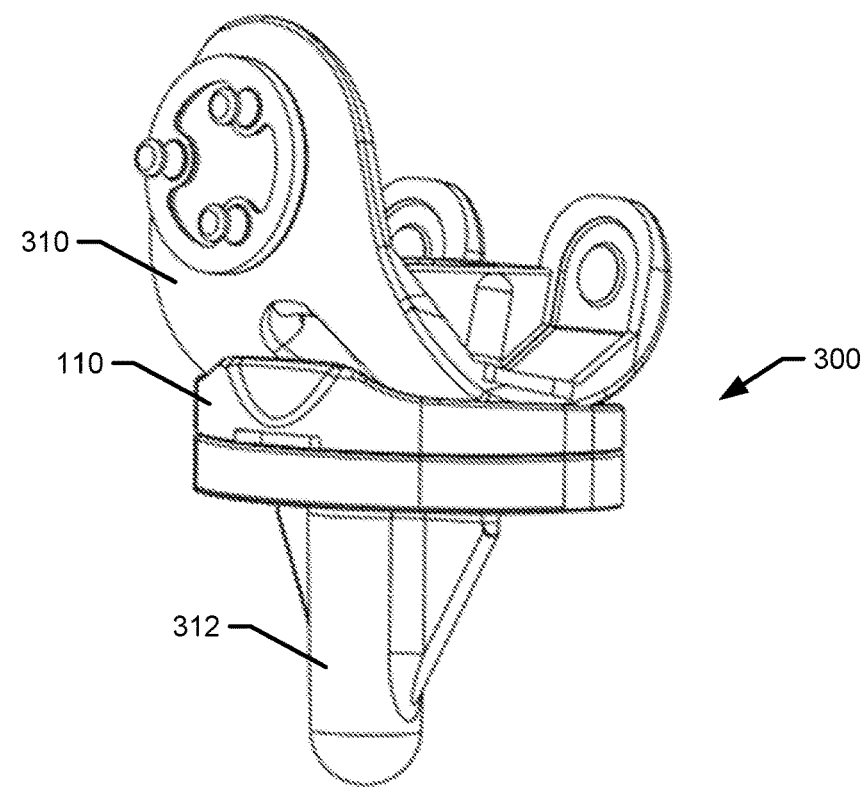
FIG. 3A illustrates an isometric view of a knee replacement implant which includes a tibial insert having electrical components operative to electrically stimulate an electrode array to at least reduce formation of a biofilm while implanted in a patient, according to some embodiments of the present disclosure.

FIG. 3A illustrates an isometric view of a knee replacement implant 300 which includes a tibial insert 312 with the component 110 having electrical components operative to electrically stimulate an electrode array to at least reduce formation of a biofilm while implanted in a patient, according to some embodiments of the present disclosure. The tibial insert 312 has a pair of tibial trays on an upper side which are adapted to guide rotational movement of a respective pair of femoral components of a femoral attachment support 310. The tibial insert 312 has a tibial component on the lower side adapted to be cemented to a tibia of the patient.

Figure 3B:
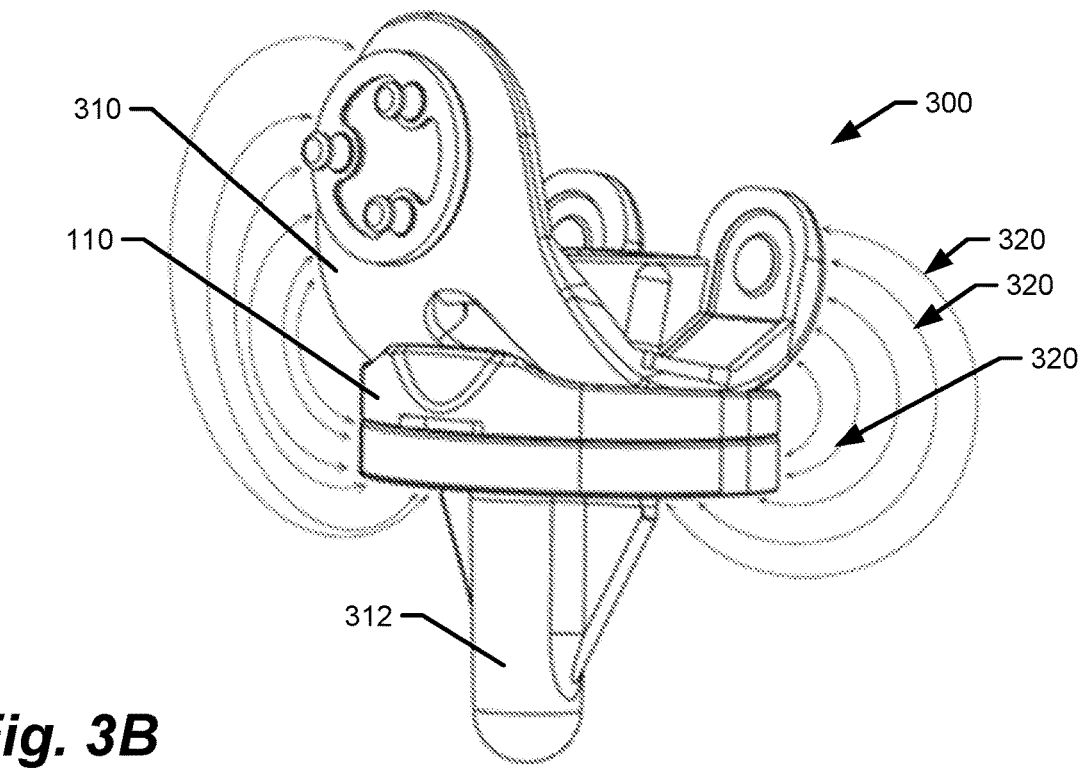
FIG. 3B illustrates electrical fields extending between locations on the knee replacement implant of FIG. 3A while the electrode array is electrically stimulated to at least reduce formation of a biofilm while implanted in a patient, according to some embodiments of the present disclosure.

FIG. 3B illustrates electrical fields 320 extending between locations on the knee replacement implant 300 of FIG. 3A while the electrode array is electrically stimulated to at least reduce formation of a biofilm while implanted in a patient, according to some embodiments of the present disclosure. Referring to FIG. 3B, a power management unit of the electronics 144 is operative to control electrical stimulation of the electrode array by current supplied by the energy storage device to be at a level which at least reduces formation of a biofilm on at least part of the implant component while implanted in the patient. The power management unit provides a voltage differential between electrodes of the electrode array to cause electric fields 320 to extend therebetween, and controls the level of current density therebetween to at least reduce formation of a biofilm and/or to at least partially eradicate a biofilm on at least part of the implant component while implanted in the patient.

Figure 4A:
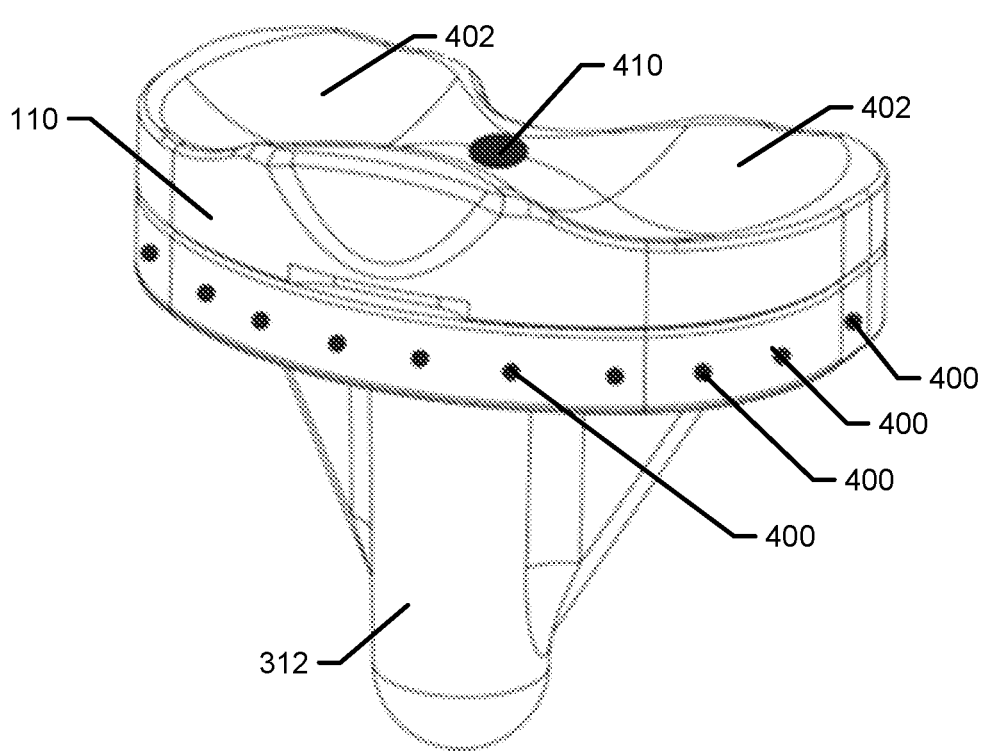
FIG. 4A illustrates an isometric view of a tibial insert with an electrode array that includes electrodes spaced apart on a side surface and a centrally located electrode, according to some embodiments of the present disclosure.

FIG. 4A illustrates an isometric view of the tibial insert 312 with an electrode array that includes electrodes 400 spaced apart on a side surface and a centrally located electrode 410, according to some embodiments of the present disclosure. Referring to FIG. 4A, the tibial insert 312 includes a pair of tibial trays 402 in the upper side which are adapted to guide rotational movement of respective pair femoral components. The electrode 410 is centrally located between the tibial trays 402. Although the electrodes in FIG. 4A and in other figures are illustrated as being exposed to adjacent tissue, e.g., formed on an external side surface of the component or exposed through an external side surface, they may instead be covered by a material which allows electrical fields to pass through, e.g., an electrically insulative material or substantially non-conductive material.

Figure 4B:
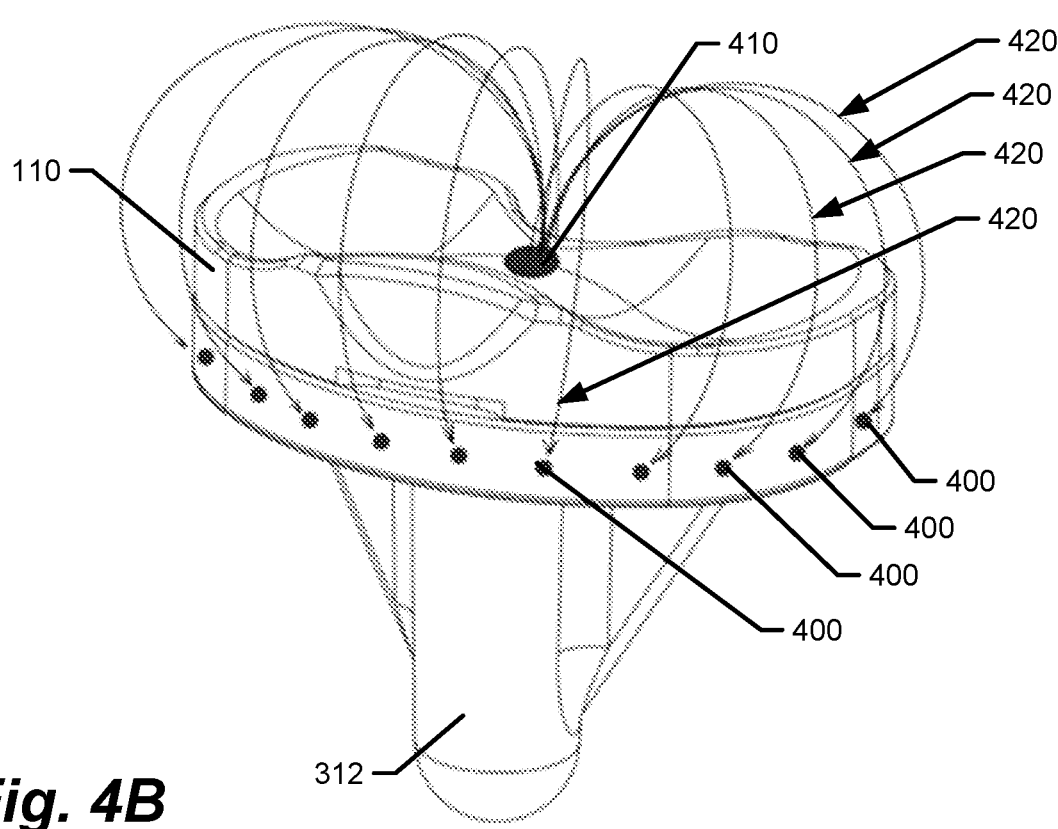
FIG. 4B illustrates electrical fields extending between the electrodes on the side surface and the centrally located electrode while the electrode array of FIG. 4A is electrically stimulated, according to some embodiments of the present disclosure.

FIG. 4B illustrates electrical fields 420 extending between the electrodes 400 on the side surface and the centrally located electrode 410 while the electrode array of FIG. 4A is electrically stimulated, according to some embodiments of the present disclosure. The power management unit provides a voltage differential between the central electrode 410 and the side electrodes 400 of the electrode array to cause electric fields 420 to extend therebetween, and controls the level of current density therebetween to at least reduce formation of a biofilm and/or to at least partially eradicate a biofilm on at least part of the implant component while implanted in the patient.

Figure 5A:
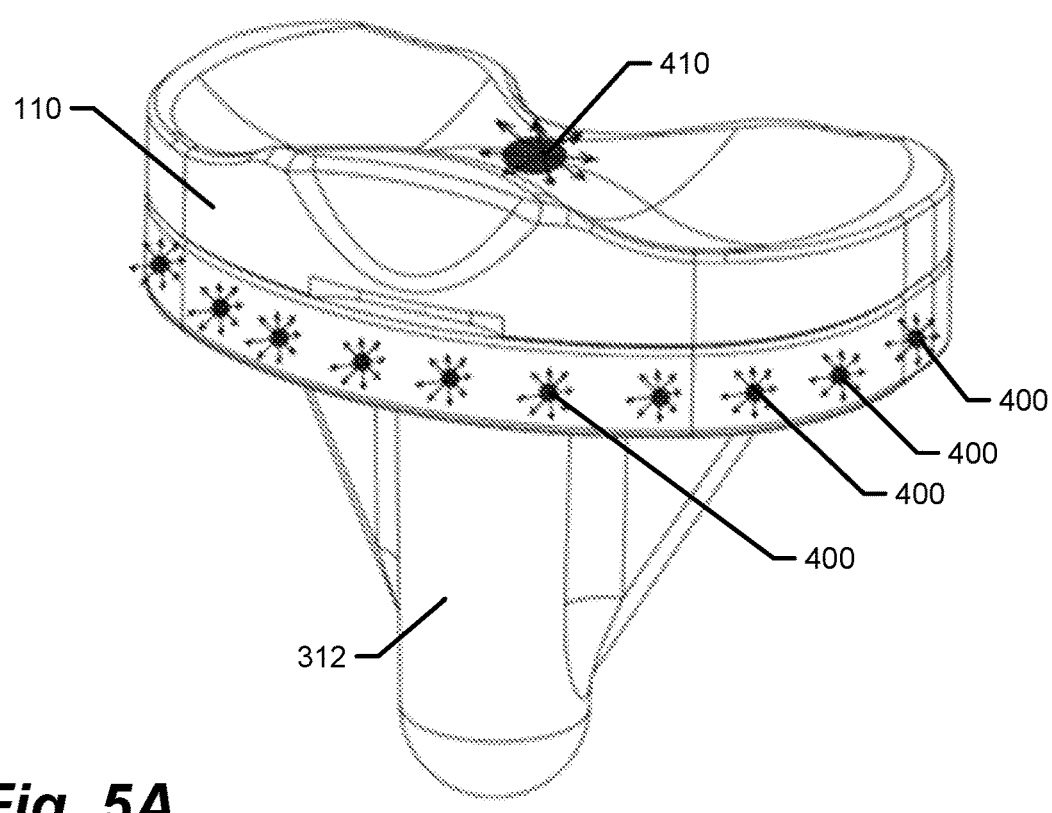
FIG. 5A illustrates an isometric view of a tibial insert with another electrode array that includes electrodes spaced apart on a side surface and a centrally located electrode, according to some embodiments of the present disclosure.

FIG. 5A illustrates an isometric view of the tibial insert 312 with another electrode array that includes electrodes 400 spaced apart on a side surface and a centrally located electrode 410, according to some embodiments of the present disclosure.

Figure 5B:
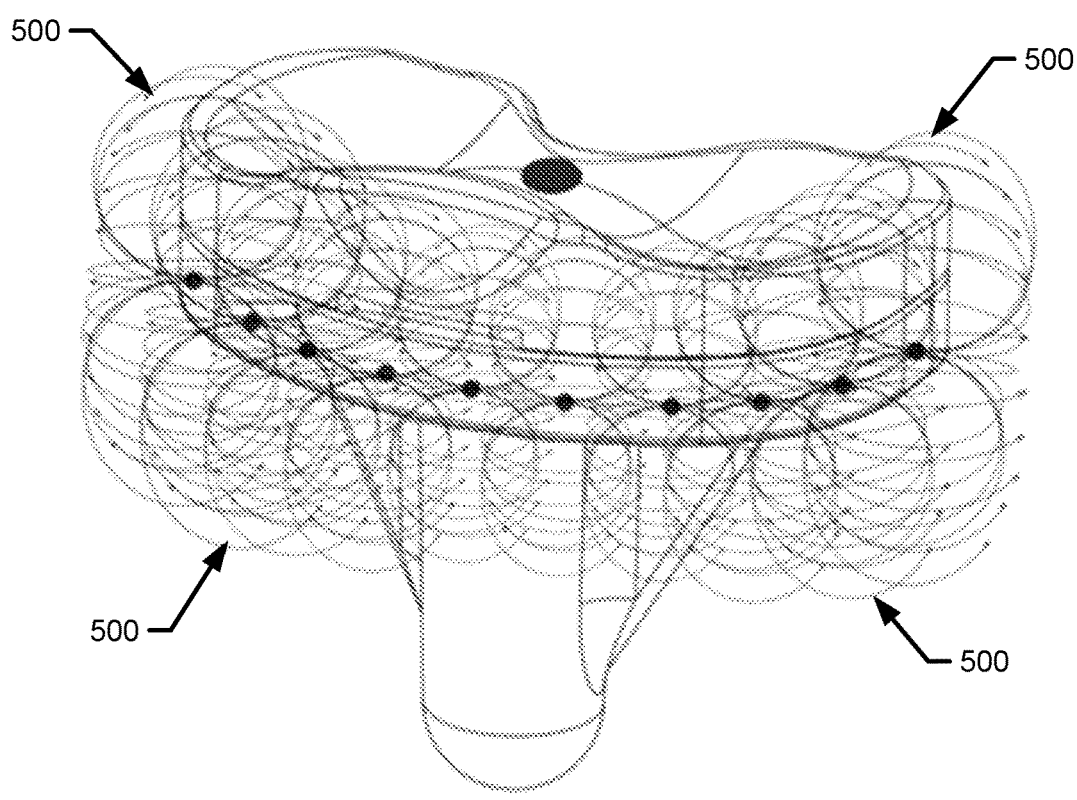
FIG. 5B illustrates electrical fields extending between the electrodes on the side surface and the centrally located electrode while the electrode array of FIG. 5A is electrically stimulated, according to some embodiments of the present disclosure.

FIG. 5B illustrates electrical fields 500 extending between the electrodes 400 on the side surface and extending between the centrally located electrode 410 the electrodes 400 on the side surface while the electrode array of FIG. 5A is electrically stimulated, according to some embodiments of the present disclosure. In contrast to the electrical fields illustrated in FIG. 4B, the electrical fields 500 also extend between various of the electrodes 400 on the side surface by the electronics 114 generating sufficient voltage potentials between the various of the electrodes 400 on the side surface.

FIG. 6 illustrates an isometric view of tibial insert 312 showing a cross-sectional line A-A which extends through an embedded energy storage device and electronics which operate according to some embodiments of the present disclosure.

FIG. 7 illustrates a cross-sectional view along line A-A of the tibial insert 312 of FIG. 6 which exposes two sealed enclosures 700 (e.g., 116 in FIG. 1) and 710 collectively containing an embedded energy storage device and electronics including a power management unit, controller, and sensors according to some embodiments of the present disclosure. In one embodiment, enclosure 700 hermetically seals the electronics 114. The other enclosure 710 may hermetically seal the energy storage device, which is now illustrated as having a cylindrical configuration instead of the rectangular configuration of device 112 in FIG. 1.

FIG. 8 illustrates the tibial insert of FIG. 7 with the enclosures 700 and 710 removed to expose an arrangement of the embedded energy storage device 810 and electronics 114 including a circuit board a power management unit, controller, and sensors according to some embodiments of the present disclosure.

FIG. 9A illustrates a top view of the component of the tibial insert 110 of FIG. 6 configured according to some embodiments of the present disclosure. Referring to FIG. 9A, the component has a pair of tibial trays on an upper side adapted to guide rotational movement of a respective pair of femoral components of the femoral attachment support 310 (FIG. 3A), and having a tibial component on a lower side adapted to be cemented to a tibia of the patient. Pairs of electrodes are formed in each of the tibial trays. A first electrode 900a and a second electrode 910a are on (in) one of the tibial trays. The first electrode 900a at least partially encircles and is electrically isolated from the second electrode 910a. A third electrode 900b and a fourth electrode 910b on (in) the other one of the tibial trays. The third electrode at least partially encircles and is electrically isolated from the fourth electrode 910b.

Although the first and third electrodes 900a, 900b are illustrated an completed encircling respective ones of the second and fourth electrodes 910a, 910b, the first and third electrodes 900a, 900b may instead only at least partially encircle, e.g., at least 50% around, the respective ones of the second and fourth electrodes 910a, 910b.

In one embodiment, the first electrode 900a has a continuous elongated shape, e.g., curved line, at least partially encircling a majority of the second electrode 910a. Similarly, the third electrode 900b has a continuous elongated shape at least partially encircling a majority of the fourth electrode 910b.

In another embodiment, the first electrode 900a includes a plurality of conductive segments that are electrically coupled and spaced apart along a path which at least partially encircles a majority of the second electrode 910a. Similarly, the third electrode 900b includes a plurality of conductive segments that are electrically coupled and spaced apart along a path which at least partially encircles a majority of the fourth electrode 910b.

The power management unit of electronics 144 is operative to control current density through patient tissue between the first electrode 900a and the second electrode 900b while electrically stimulated by the energy storage device 112,810. Similarly, the power management unit of electronics 144 is operative to control current density through patient tissue between the third electrode 900b and the fourth electrode 910b while electrically stimulated by the energy storage device 112,810.

FIG. 9B illustrates electrical fields extending between the electrodes of FIG. 9A while electrically stimulated, according to some embodiments of the present disclosure. Referring to FIG. 9B, the power management unit of the electronics 144 is operative to control electrical stimulation of the electrode array by current supplied by the energy storage device to be at a level which at least reduces formation of a biofilm on at least part of the implant component while implanted in the patient. The power management unit provides a voltage differential between the first and second electrodes 900a, 910a to cause electric fields 920a to extend therebetween, and controls the level of current density therebetween to at least reduce formation of a biofilm and/or to at least partially eradicate a biofilm on at least part of the implant component while implanted in the patient. Similarly, the power management unit provides a voltage differential between the third and fourth electrodes 900b,910b to cause electric fields 920b to extend therebetween, and controls the level of current density therebetween to at least reduce formation of a biofilm and/or to at least partially eradicate a biofilm on at least part of the implant component while implanted in the patient.

FIG. 10 illustrates components of a medical implant which are interconnected and configured to operate according to some embodiments of the present disclosure.

Referring to FIG. 10, a hermetically sealed electronics enclosure 1080 encloses power management unit 1000, energy storage device 1010, controller 1020, internal sensors 1040, wireless communication transceiver 1060, energy generation circuit 1070, and system shutdown switch 1080. The implant further includes electrode array 1030 having a plurality of electrodes, e.g., electrode_1 (1032*a*) to electrode_n (1032*n*), and may include external sensors 1050. The controller 1020 may include one or more processor circuits ("processor") which execute instructions stored in one or more memory circuits ("memory").

The power management unit 1000 is operative to control electrical stimulation of the electrode array 1030 by current supplied by the energy storage device 1010 to be at a level which at least reduces formation of a biofilm on at least part of the implant component while implanted in the patient. For example, as discussed above, power management unit 1000 can be operative to control current density through patient tissue between the at least two electrodes of the electrode array 1030 while it is electrically stimulated by the energy storage device 1010. Controller 1020 is operative to control duration of the electrical stimulation of the electrode array 1030 by the power management unit 1000.

The power management unit 1000 may operate in various different modalities, two of which can include a preventative modality and an eradication modality. The preventative modality is adapted to reduce or prevent formation of a biofilm on the implant component by electrical stimulation of the electrode array 1030 which induces bacteria to remain free-floating where it is vulnerable to a patient's immune responses and antibiotics. The eradication modality is adapted to reduce or remove a biofilm which has formed on the implant component by electrical stimulation of the electrode array 1030.

The prevention modality may stimulate the electrode array 1030 with a relatively low current output over a relatively long period of time in a constant current control configuration. For example, the power management unit 1000 may be operative during the prevention modality to control the control current density to be in a range from 0.001 mA/mm^2 to 0.01 mA/mm^2. The controller 1020 may be operative during the prevention modality to control the duration of the electrical stimulation to be in a range from 8 hours to 24 hours.

The eradication modality may stimulate the electrode array 1030 with a relatively high current output over a relatively short period of time in a constant current control configuration. The eradication modality may be carried out without or without a concurrent antibiotic treatment of a patient, such as where stimulation of the electrodes while the patient is undergoing antibiotic treatment is used to enhance the effectiveness of the antibiotics at eradicating biofilm on the implant component. In one embodiment, the power management unit 1000 is operative during the prevention modality to control the control current density to be in a range from 0.01 mA/mm^2 to 0.1 mA/mm^2. Controller 1020 may be operative during the eradication modality to control the duration of the electrical stimulation to be in a range from 1 minute to 8 hours.

In one embodiment, the power management unit 1000 is operative to control the current density to be a level sufficient to form hydrogen bubbles through reaction with the patient tissue and dislodge biofilm on a surface of the implant component. The power management unit 1000 may cause a burst dose of current through the electrode array 1030 to form hydrogen bubbles through an electrochemical reaction at the interface of the biofilm and a cathodic surface when a sufficient level of direct current voltage is applied. These bubbles mechanically separate the biofilm from the associated surface, fragment the polymerized matrix, and eject the bacterial cells. The electrochemical disinfection can directly kill bacteria through an electricidal effect.

The power management unit 1000 may be operative to control a current waveform supplied to at least one of the electrodes during at least a majority of the duration of the electrical stimulation, to be one of: a constant directed current; a discontinuous pulsed direct current; and a discontinuous alternating direct current. Alternatively, the power management unit 1000 may be operative to control the will current waveform during at least a majority of the duration of the electrical stimulation, to be a continuous sinusoidal alternating current.

The stimulation modality may be independent of the electrode configuration and design, meaning that both the prevention and eradication modalities may be performed through a shared electrode array 1030. The electrode array 1030 may include one or more sets of electrodes in, e.g., a 2- or 3-electrode configuration. The 2-electrode configuration can be supplied current to operate one as an anode and the other as a cathode. The 3-electrode configuration can include a working electrode, reference electrode, and counter electrode.

Sets of electrodes of electrode array 1030 may be patterned on the surfaces of the implant components linearly or radially. The electrodes may also be configured in a dot matrix, nested zig-zags, nested spirals, etc. The electrodes may be constructed of a biocompatible implant material such as TAV or stainless steel, a noble metal such as gold, silver, or platinum, or a carbon-based material such as graphite or graphene. The electrodes may be configured in a subassembly that is adhered to or embedded within the surface of the implant components. In addition, the electrodes may be formed by printing or depositing a conductive layer on the surface of the implant components or in a dielectric configuration with a layer of insulative ink between the implant surface and conductive ink.

The internal sensors 1040 and/or external sensors 1050 can provide sensor feedback which can be used by controller 1020 to generate reports which are transmitted through the wireless communication transceiver 1060 via one or more wireless access points 1110 to a network computing resource 1130 (FIG. 11) and/or to a patient computing device 1102 (e.g., smartphone, tablet computer, laptop computer, desktop computer, etc.) executing an application. The sensor feedback may indicate conditions which are analyzed to provide non-invasive characterization of presence of and/or amount (e.g., thickness, area, volume, density, etc.) of microbial biofilms.

The networked computing resource 1130, patient computing device 1102, and/or other networked component may provide a command to the controller 1020 to activate or deactivate one or more operational modalities, e.g., eradication modality and/or prevention modality. Alternatively or additionally, controller 1020 may be configured to activate one or more operational modalities, e.g., eradication modality and/or prevention modality, based on determining that sensor feedback satisfies a defined rule for presence of a threshold level of biofilm formation on the implant component. Similarly, controller 1020 may be configured to deactivate one or more operational modalities, e.g., eradication modality and/or prevention modality, based on determining that sensor feedback satisfies a defined rule for no presence of or less than a threshold level of biofilm formation on the implant component.

Controller 1020 may monitor sensor feedback to provide early detection of periprosthetic joint infection by directly measuring the development of infection-causing biofilm. In addition, controller 1020 may measure the state and rate of biofilm growth to provide clinical feedback on the effectiveness of treatment provided by the implant and antibiotic therapy.

Non-invasive characterization of microbial biofilms and characterization of operation of the medical implant and/or events which may indication damage of the implant can be performed using the internal sensors 1040 and/or the external sensors 1050.

The internal sensors 1040 and/or external sensors 1050 can include a temperature sensor 1042, 1052 operative to output a temperature signal indicative of temperature at a surface of the implant component. The controller 1020 can be operative to communicate temperature data based on the temperature signal through the wireless communication transceiver 1060, and to initiate electrical stimulation of the electrode array 1030 by the power management unit 1000 based on an activation command received through the wireless communication transceiver 1060. In another embodiment, the controller 1020 is operative to initiate electrical stimulation of the electrode array 1030 by the power management unit 1000 based on a level of the temperature indicated by the temperature signal satisfying an eradication modality initiation rule. In another embodiment, the controller 1020 is operative to initiate electrical stimulation of the electrode array 1030 by the power management unit 1000 based on an observed trend over time in levels of the temperature indicated by the temperature signal satisfying an eradication modality initiation rule (e.g., sensed temperature increase profile indicative of infection).

The temperature signal may be monitored during wireless charging of the energy storage device 1010 by the energy generation circuit 1070, e.g., by wireless power transfer through inductive coupling or resonant inductive coupling with an external charging transmitter device, to prevent excessive temperatures which may damage tissue or electronics. The temperature signal may characterize heating caused by friction generated while moving and loading the an implant joint during activities, and/or characterize heating caused by biological processes such as inflammation as a biomarker for complications such as infection.

The internal sensors 1040 and/or external sensors 1050 can include a pressure sensor 1044 operative to output a pressure signal indicative of pressure at a surface of the implant component and/or a force sensor 1054 operative to output a force signal indicative of force on a surface of the implant component. The controller 1020 can be operative to record the pressures indicated by the pressure signal over time and/or to record the forces indicated by the force signal over time, and to communicate a report indicating the recorded pressures and/or the recorded forces through the wireless communication transceiver 1060.

The sensor feedback from the pressure sensor 1044 and/or force sensor 1054 may be used to measure pressure/force transferred through the joint. Sensors 1044/1054 may include piezoelectric elements, strain gauges, or a load cell. The sensor feedback may be used for one or more the following analysis: quantify and display the force distribution and force magnitudes during the range of motion intraoperatively to allow the surgeon to verify properly implant placement and soft tissue balancing; measure kinetics of the joint during patient activities as a measure of mobility; measure changes in kinetics of the joint over time as a method of monitoring recovery and development of adverse events such as changes of gait due to pain; and measure changes in kinetics of the joint over time a method of monitoring implant wear and breakage.

The internal sensors 1040 and/or external sensors 1050 can include a microphone sensor 1048,1058 operative to output a microphone signal indicative of sound generated by an articulating joint formed with the implant component when articulated by the patient. Controller 1020 can be operative to record the sounds indicated by the microphone signal over time, and to communicate a report indicating the recorded sounds through the wireless communication transceiver 1060. The recorded sounds may be analyzed to identify when, for example, an articulatable implant has experienced excessive wear and/or has become damaged from movement, impact, etc. The microphone signal may be used to measure sounds generated within a joint due to the interactions between implant components. The recorded sounds may be used for one or more of the following analysis: detect squeaking sounds that may indicate high friction within the joint due to worn components or the lack of lubricious synovial fluid; detect mechanical breakage sounds that indicate failure of the implants; and detect sounds that that can indicate relative motion between the implant components and bone as an indicator of mechanical loosening.

The internal sensors 1040 and/or external sensors 1050 can include an inertial measurement unit (IMU) 1046,1056 operative to output inertial data indicative of acceleration of the implant component when moved by the patient. Controller 1020 can be operative to record the inertial data over time, and to communicate a report indicating the recorded inertial data through the wireless communication transceiver 1060. The recorded inertial data may be analyzed to identify when, for example, an articulatable implant has experienced excessive wear (e.g., experiencing excessive vibration during movement) and/or has become damaged from movement, impact, etc.

The IMU 1046, 1056 may be used for collecting motion data, including linear acceleration (accelerometer), rotational acceleration (gyroscope), and directionality of the Earth's magnetic field (magnetometer). The IMU data may be used for one or more of the following analysis: measure kinematics of the joint and patient mobility as an objective outcome measure of patient recovery, including range of motion, step count, gait, etc.; measure kinematics of the joint as a measure of implant placement for post-operative assessment of surgical execution relative to the surgical plan; measure kinematics of the joint to monitor the occurrence of adverse events including a patient fall, implant wear, mechanical breakage, infection, implant loosening, or dislocation; measure vibrations of the implant components as a measure of implant wear, implant loosening, or mechanical breakage; measure patient movements as a method to wake up (activate) the electronics from a deep sleep power saving mode; and measure compliance of postoperative recovery protocols including ambulation objectives and exercise regimens.

The external sensors 1050 can include an electrochemical sensor 1053 operative to output a signal indicative of a level of a defined chemical detected on the implant component. Controller 1020 can be operative to record the levels of the defined chemical indicated by the signal over time, and to communicate a report indicating the levels of the defined chemical through the wireless communication transceiver 1060. The recorded levels of the defined chemical may be analyzed to identify the presence of a biofilm, identify type of bacteria present in an biofilm (e.g., based on chemicals output by the bacteria), etc.

The electrochemical sensor 1053 may measure the presence and concentration of a target substance (a.k.a. analyte) by oxidizing or reducing the substance at an electrode and measuring the resulting current. Electrochemical sensor 1053 may be a three electrode configuration that includes a working electrode (where the substance is measured), a reference electrode, and a counter electrode. The working electrode may be constructed of a bare material with high electrochemical resistance, such as a noble metal (e.g. platinum) or a carbon-based material (e.g. graphene). The working electrode may also be coated with a selective membrane to form a biosensor. The selective membrane allows only reactions between the electrode and target analyte to occur. The membrane may contain various biosensing elements such as cells, microbes, cell receptors, antibodies, enzymes, or nucleic acids. In a configuration to detect the presence of bacteria, the working electrode membrane can contain antibodies of a specific bacterial species. A variety of electrochemical analysis methods may be deployed to collect data from the sensor including voltammetry, amperometry, potentiometry, and electrochemical impedance spectroscopy.

Electrochemical sensors could be used for any one or more of the following analysis: measure the presence of bacterial biofilm on the surface of implant components; characterize bacterial biofilm developed on the surface of implant components, including stage of formation (e.g. initial attachment, immature formation, mature formation), the rate of formation, and the thickness; identify the presence and concentration of specific bacterial species within the biofilm matrix, including *Staphylococcus epidermidis* and *Staphylococcus aureus*; identify the presence and concentration of specific bacterial species in the planktonic (i.e. free-floating) state within the synovial fluid and synovium that surrounds the joint components, including *Staphylococcus epidermidis* and *Staphylococcus aureus*; and identify certain biomarkers for detection of PJI within the synovial fluid that surrounds the joint components.

The identifiable biomarkers may include, without limitation, pH, leukocyte count, monocyte percentage, lymphocyte percentage, neutrophil percentage, C-reactive protein (CRP), glucose, lactate, granulocyte-macrophage colony-stimulating factor, interferon-γ, interleukin-1β (IL-1β), IL-2, IL-4, IL-5, IL-6, IL-8, IL-10, IL-12p70, IL-13, IL-17A, IL-23, tumor necrosis factor-α, α-defensin, and leukocyte esterase.

To identify the concentration of biocidal molecules generated from electrochemical reactions during the stimulation process. These biocidal molecules can include hydrogen peroxide and hypochlorous acid. The stimulation may be controlled by the power management unit 1000 and controller 1020, and/or the networked computing resource 1130 and/or patient device 1102 in a semi-autonomous or autonomous control loop that throttles the dose and duration of stimulation treatment to limit the production of biocidal molecules to levels that kill bacteria but which do not exceed levels that cause excessive toxic reactions with surrounding tissues.

The internal sensors 1040 and/or external sensors 1050 may include an optical sensor 1057 which provides sensing used to measure optical characteristics of the implant, synovial fluid, and surrounding tissue. The optical sensor 1057 may be used for one or more of the following analysis: measure characteristics of the synovial fluid through Spectrophotometry methods; measure the turbidity and color of the synovial fluid; measure the presence of biofilm developed on the surface of the sensor; and measure the presence of bacterial species. Some bacterial species fluoresce in the presence of UV light. The optical sensor may be operative to emit a UV pulse and measure the intensity of returned light at specific wavelengths to detect the concentration and presence of specific bacteria.

The system shutdown switch 1080, e.g., a Reed switch, may be used as a master on/off switch for the system.

The energy generation circuit 1070 can be configured to provide energy to recharge the energy storage device 1010. Energy generation circuit 1070 can contain components operable for harvesting energy, receiving wirelessly transferred energy, and recharging the energy storage device.

Energy generation circuit 1070 may contain an inductive charging coil to receive wireless power transferred through inductive coupling or resonant inductive coupling methods with an external charging transmitter device. The external charging transmitter coil may be embedded within a wearable brace, clothing element, or as a standalone device that can be adhered to the relevant location on the skin.

Energy generation circuit 1070 may contain an RF antenna to receive wireless power transferred through RF wireless power transfer methods with an external charging transmitter device. The external transmitter may be a dedicated device that can be set up within the vicinity of the patient within their home or workplace. The external transmitter could also be integrated within a non-slip pad that could be mounted to the top of the patient's mattress or other furniture to charge the smart implant device while they sleep or sit.

Energy generation circuit 1070 may contain: an RF antenna to harvest wireless power from ambient RF radiation; a piezoelectric stack to harvest power through cyclical loading of the joint during ambulation; and/or a thermoelectric energy harvesting cell to harvest power from thermal gradients across the joint and implant components.

The wireless communication transceiver 1060 contains electronic components operative for wireless communication with external devices such as mobile phones, tablet computers, home base stations, networked computing resources (cloud resources) and/or computing servers operated by clinicians. Wireless communication transceiver 1060 may include a wireless communication microcontroller unit 1062 which communicates through a wireless communication antenna 1064. Secure (encrypted) communications may be provided through operation of a cryptography chip (circuit) 1066. Wireless communications may be performed using any relatively low power communication protocol, such as Bluetooth or Bluetooth Low Energy (2.4 GHz), medical implant communications system (MICS) at about 400 MHz, or some other RF frequency communication protocol.

FIG. 11 illustrates a system that includes a network computing resource 1130, wireless communication access point 110, medical implant and other elements which are interconnected and configured to operate according to some embodiments of the present disclosure.

Referring to FIG. 11, example data flows are illustrated between system elements according to some operations of a smart implant which is operative to measure patient mobility (e.g., step count), intra-joint health (e.g., temperature), and adverse events (e.g., falls or other impacts). In the example embodiment, a high temperature event is identified and can be interpreted as a sign of patient 1100 infection associated with the implant. A clinician may use a high temperature alert from the implant in combination with other sensor feedback, symptoms, and tests to diagnose the patient with an infection. The clinician may then choose to remotely deliver stimulation treatment within the joint using the smart implant as a standalone treatment or in combination with an antibiotic therapy, by a treatment activation command/signal communicated to the controller 1020 to initiate electrical stimulation of the electrode array for a therapeutic response at one or more levels (e.g., identified based on the treatment activation command/signal) controlled by the power management unit 1000.

More generally, the care team can view senor feedback and other reported data, such as device status or biofilm measurements, on their clinician dashboard, which can be accessed through a web browser on a computer. Through this dashboard, the clinician may have the ability to remotely deliver a burst stimulation treatment. In addition, the patient also has access to more high-level information about their device and treatment history through a patient mobile application on device 1102. Depending on the timing of adjacent connectivity and continuum of care projects, this functionality may be integrated into a single patient engagement app and care management platform rather than as separate, purpose-built applications.

The illustrated implant includes an electronics module 820 that includes a controller 1020, IMU 1046, temperature sensor 1042, and BLE communication module 1060. The controller 1020 can include program code which includes an embedded machine learning (ML) model 1022 operative to determine if sensor data is indicative of a reportable event and/or satisfies a therapeutic modality initiation rule which may automatically trigger initiation of therapeutic stimulation of the electrode array 1030 and/or reporting of a request for therapeutic authorization.

In one embodiment, the ML model 1022 is operative to trigger reporting when sensed temperature over time indicates infection (e.g., temperature profile indicative of infection growth), when sensed acceleration indicates a fall or excessive impact, etc. Alternatively or additionally, simpler action logic 1024 may operate to output an event signal when sensed temperature exceeds a defined threshold.

The access point 1110 operates as a communication link between the smart implant and other elements of the system, e.g., the network computing resource(s) 1130, patient electronic device 1102 (e.g., smart phone, tablet computer, etc.), clinician dashboard 1140, emergency contact person 1120. In one embodiment, the access point 1110 includes a controller 1116 with a BLE communication module 1118 operative to communicate with the BLE communication module 1060 of the implant. The access point 1110 can include another microcontroller 1112 with a Wi-Fi module 1114 operative to relay communications between the BLE communication module 1118 and other elements of the system via Wi-Fi communications.

Further Definitions and Embodiments

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality)

and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following examples of embodiments and their equivalents, and shall not be restricted or limited by the foregoing detailed description.

What is claimed is:

1. The medical implant comprising:
an implant component configured to be implanted in a patient;
an electrode array comprising at least two electrodes spaced apart on the implant component;
an energy storage device inside the implant component; and
a power management unit inside the implant component and operative to control electrical stimulation of the electrode array by current supplied by the energy storage device to be at a level which at least reduces formation of a biofilm on at least part of the implant component while implanted in the patient,
wherein the implant component comprises a tibial insert having a pair of tibial trays on an upper side adapted to guide rotational movement of a respective pair of femoral components of the medical implant, and having a tibial component on a lower side adapted to be cemented to a tibia of the patient,
the first set of the electrodes of the electrode array are spaced apart on a side surface of the tibial insert;
the second set of at least one of the electrodes comprises a centrally located electrode between the tibial trays; and
the power management unit is operative to control current density through patient tissue between the first set of the electrodes and the centrally located electrode while electrically stimulated by the energy storage device.

2. The medical implant of claim 1, wherein:
the electrode array comprises:
a first electrode and a second electrode on one of the tibial trays, the first electrode at least partially encircling and electrically isolated from the second electrode, and
a third electrode and a fourth electrode on the other one of the tibial trays, the third electrode at least partially encircling and electrically isolated from the fourth electrode; and
wherein the power management unit is operative to control current density through patient tissue between the first electrode and the second electrode while electrically stimulated by the energy storage device, and to control current density through patient tissue between the third electrode and the fourth electrode while electrically stimulated by the energy storage device.

3. The medical implant of claim 2, wherein:
the first electrode has a continuous elongated shape at least partially encircling a majority of the second electrode; and
the third electrode has a continuous elongated shape at least partially encircling a majority of the fourth electrode.

4. The medical implant of claim 2, wherein:
the first electrode comprises a plurality of conductive segments electrically coupled and spaced apart along a path at least partially encircling a majority of the second electrode; and
the third electrode comprises a plurality of conductive segments electrically coupled and spaced apart along a path at least partially encircling a majority of the fourth electrode.

5. The medical implant of claim 1, further comprising:
a wireless communication transceiver;
a temperature sensor operative to output a temperature signal indicative of temperature at a surface of the implant component; and
a controller operative to communicate temperature data based on the temperature signal through the wireless communication transceiver, and to initiate electrical stimulation of the electrode array by the power management unit based on an activation command received through the wireless communication transceiver.

6. The medical implant of claim 5, wherein:
the controller is further operative to initiate electrical stimulation of the electrode array by the power management unit based on a level of the temperature indicated by the temperature signal satisfying an eradication modality initiation rule.

7. The medical implant of claim 5, wherein:
the controller is further operative to initiate electrical stimulation of the electrode array by the power management unit based on an observed trend over time in levels of the temperature indicated by the temperature signal satisfying an eradication modality initiation rule.

8. The medical implant of claim 1, further comprising:

a wireless communication transceiver;

a pressure sensor operative to output a pressure signal indicative of pressure at a surface of the implant component and/or a force sensor operative to output a force signal indicative of force on a surface of the implant component; and a controller operative to record the pressures indicated by the pressure signal over time and/or to record the forces indicated by the force signal over time, and to communicate a report indicating the recorded pressures and/or the recorded forces through the wireless communication transceiver.

9. The medical implant of claim 1, further comprising:

a wireless communication transceiver;

a microphone sensor operative to output a microphone signal indicative of sound generated by an articulating joint formed with the implant component when articulated by the patient; and a controller operative to record the sounds indicated by the microphone signal over time, and to communicate a report indicating the recorded sounds through the wireless communication transceiver.

10. The medical implant of claim 1, further comprising:

a wireless communication transceiver;

an inertial measurement unit operative to output inertial data indicative of acceleration of the implant component when moved by the patient; and a controller operative to record the inertial data over time, and to communicate a report indicating the recorded inertial data through the wireless communication transceiver.

\* \* \* \* \*